United States Patent
Coates et al.

(10) Patent No.: US 6,660,345 B2
(45) Date of Patent: Dec. 9, 2003

(54) THERMOCHROMIC LIQUID CRYSTALLINE MEDIUM

(75) Inventors: David Coates, Dorset (GB); David Bishop, Corfe Mullen (GB); Robert Hammond-Smith, Fordingbridge (GB)

(73) Assignee: Merck Patent Gesellschaft Mit Beschränkter Haftung, Darmstadt (DE)

(*) Notice: Subject to any disclaimer, the term of this patent is extended or adjusted under 35 U.S.C. 154(b) by 0 days.

(21) Appl. No.: 10/246,528

(22) Filed: Sep. 19, 2002

(65) Prior Publication Data

US 2003/0052305 A1 Mar. 20, 2003

Related U.S. Application Data

(63) Continuation of application No. 09/654,926, filed on Sep. 5, 2000, now abandoned.

(30) Foreign Application Priority Data

Sep. 3, 1999 (EP) .............................................. 99116850

(51) Int. Cl.$^7$ ........................ C09K 19/52; C09K 19/32; C09K 19/34; C09K 19/38; C09K 19/12; C09D 11/00

(52) U.S. Cl. ..................... 428/1.1; 428/1.3; 252/299.01; 252/299.61; 252/299.62; 252/299.64; 252/299.67; 252/299.7; 106/31.03; 106/31.13; 106/31.72; 106/31.96

(58) Field of Search ................. 252/299.01, 299.61, 252/299.62, 299.66, 299.64, 299.67, 299.7; 428/1.1, 1.31; 106/31.03, 31.13, 31.72, 31.96; 349/106

(56) References Cited

U.S. PATENT DOCUMENTS

| | | | |
|---|---|---|---|
| 4,741,859 A | 5/1988 | McDonnell et al. | |
| 5,188,815 A | 2/1993 | Coates et al. | |
| 5,290,477 A | 3/1994 | Kondo et al. | |
| 5,651,918 A | 7/1997 | Scherowsky et al. | |
| 5,705,093 A | 1/1998 | Coates et al. | |
| 6,217,792 B1 | 4/2001 | Parri et al. | |
| 6,319,963 B1 | 11/2001 | Coates et al. | |
| 6,417,902 B1 * | 7/2002 | Greenfield et al. | 349/115 |
| 6,420,001 B1 * | 7/2002 | Coates et al. | 428/1.1 |
| 6,421,107 B1 * | 7/2002 | Greenfield et al. | 349/115 |

FOREIGN PATENT DOCUMENTS

| | | |
|---|---|---|
| EP | 0 423 293 B1 | 4/1993 |
| EP | 0 386 198 B1 | 10/1993 |
| EP | 0 564 959 A1 | 10/1993 |
| GB | 2 280 681 A | 2/1995 |

* cited by examiner

Primary Examiner—Shean C. Wu
(74) Attorney, Agent, or Firm—Millen, White, Zelano & Branigan, P.C.

(57) ABSTRACT

The invention relates to a thermochromic liquid crystalline medium comprising a liquid crystalline host component and an active component, to a thermochromic ink comprising such a thermochromic liquid crystalline medium encapsulated in a light transmissive polymeric material, to the use of a thermochromic medium or ink in decorative applications like pigments, inks and paints, cosmetics, thermodiagnostic applications like medical thermography, thermometry, optical and electrooptical applications, and security applications and devices, to a security marking or device comprising a thermochromic liquid crystalline medium or thermochromic ink and to a document of value comprising such a security marking.

22 Claims, No Drawings

THERMOCHROMIC LIQUID CRYSTALLINE MEDIUM

This application is continuation of U.S. Ser. No. 09/654,926, filed Sept. 5, 2000 now abandoned.

The invention relates to an improved thermochromic liquid crystalline medium. The invention also relates to a thermochromic ink comprising a thermochromic liquid crystalline medium encapsulated in a light transmissive polymeric material. The invention further relates to the use of a thermochromic liquid crystalline medium or ink in decorative applications like pigments, inks and paints, cosmetics, thermodiagnostic applications like medical thermography, thermometry, optical and electrooptical applications, and security applications and devices. The invention also relates to a security marking or device comprising a thermochromic liquid crystalline medium or thermochromic ink, in particular a security marking or device comprising two thermochromic liquid crystalline media or inks that differ in their chirality to produce a hidden effect, and to a document of value comprising such a security marking. Further aspects of the invention are discussed below.

BACKGROUND OF THE INVENTION

Thermochromic liquid crystal materials, such as thermochromic compounds or compositions are characterized in that they show a visible colour change upon temperature variation. One well known class of thermochromic materials are specific types of cholesteric liquid crystals (CLCs). CLCs exhibit a helically twisted molecular structure wherein the pitch p of the molecular helix is related to the reflected wavelength $\lambda$ and the average refractive index n of the liquid crystal by equation (1)

$$\lambda = n \cdot p \tag{1}$$

In thermochromic CLCs the reflection wavelength $\lambda$ shows a significant temperature dependence. If the reflected wavelength is inside the visible range, the thermochromic CLC material undergoes a visible colour change upon variation of the temperature. As the cholesteric liquid crystals are optically birefringent, they typically do not reflect a single wavelength, but a narrow band of wavelengths wherein the bandwidth $\Delta\lambda$ is defined according to equation (2)

$$\Delta\lambda = \Delta n \cdot p \tag{2}$$

with $\Delta n$ being the birefringence of the liquid crystal material.

The above described thermochromic effect is exploited in a wide range of applications, such as decorative applications like pigments, inks or paints, cosmetics, thermodiagnostic applications like medical thermography, thermometry, optical and electrooptical applications, and security markings and devices.

For the above mentioned applications, typically cholesteric liquid crystalline compositions are used comprising achiral and chiral liquid crystalline or mesogenic compounds, which are encapsulated as small droplets in light transmissive polymer microcapsules, for example of gelatine or gum arabic, or in a continuous matrix of a transparent binder polymer.

In order to exhibit thermochromic behaviour, the cholesteric liquid crystalline composition should exhibit a cholesteric phase and an underlying smectic phase, i.e. a smectic phase below the temperature range of the cholesteric phase.

Thermochromic compositions are disclosed for example in EP 0 386 198, EP 0 423 293, EP 0 564 959 and GB 2 280 681.

However, the thermochromic compositions of prior art have several drawbacks. Thus, the thermochromic materials known in the prior art do often exhibit thermochromic colour play only in a narrow temperature range.

Therefore, to achieve a satisfying thermochromic effect in prior art thermochromic mixtures often a large amount of chiral components is needed, which in some cases make up more than 50% by weight of the total mixture.

On the other hand, it is generally desired to reduce the amount of chiral components in a liquid crystal mixture for several reasons. Thus, chiral compounds do often reduce the mesophase range and clearing point of a liquid crystal mixture. Furthermore, the preparation of chiral compounds with high enantiomeric purity is often difficult and expensive. Also, chiral compounds for liquid crystalline mixtures are usually not available in the same broad variety like e.g. nematic compounds. Thus, when the chiral compounds make up a large part of the mixture it is difficult to vary the composition of the mixture in order to adapt its properties to specific requirements. Finally, due to the presence of high amounts of chiral compounds it is often difficult to achieve mixtures with a high birefringence.

Another feature of CLC's is their ability to reflect circularly polarised light. The state of polarisation of light reflected depends upon the "handedness" of the helical structure formed within the thermochromic liquid crystalline medium, which is itself determined by the structure of the chiral compound(s) used in the mixture.

SUMMARY OF THE INVENTION

The above mentioned effect can be exploited in security markings and devices by providing a "hidden" effect. By using two thermochromic liquid crystalline media that differ only by their chirality, i.e. by the total twist sense of their chiral component that can be made up by one or more chiral compounds, a hidden design could be produced when the device is viewed through a suitable circular polariser.

Thus, it was an aim of the invention to provide thermochromic media which show a colour change over a wide temperature range, including room temperature or temperatures close to room temperature, and which do not contain high amounts of chiral compounds.

The inventors have found that the above aim can be achieved by providing thermochromic media according to the present invention. The inventive media are characterized in that they comprise a liquid crystalline host mixture with a nematic phase and an underlying smectic phase, to which a small amount of an optically active component is added, wherein said optically active component comprises one or more chiral dopants with a high helical twisting power (HTP).

The HTP of a chiral dopant describes its ability to induce or enhance a helical twist in a medium consisting of a liquid crystalline host mixture and the dopant. The HTP is defined by equation (3)

$$HTP = (p \cdot c)^{-1} \tag{3}$$

wherein p is the helical pitch p (in $\mu$m) and c the concentration (in % by weight) of the chiral dopant in the medium.

The inventors have found that, when using chiral compounds with a high HTP of at least $20\,\mu m^{-1}$ already in small amounts in a liquid crystal host mixture, it is possible to obtain a thermochromic medium with a wide temperature range of the thermochromic colour play. Furthermore it was found that by using these dopants, it is possible to provide a thermochromic medium wherein the width and position of the temperature range of the thermochromic colour play can easily be controlled by careful selection of the amount and HTP of the chiral compounds and of the smectic-nematic phase transition temperature ($T_{S-N}$) of the host mixture.

One object of the invention is a thermochromic liquid crystalline medium comprising a liquid crystalline host mixture and an optically active component, characterized in that the liquid crystalline host mixture has a smectic—nematic phase transition temperature in the range from about 0 to 60° C. and the optically active component comprises at least one chiral dopant having a helical twisting power (HTP) of at least 20 $\mu m^{-1}$.

Another object of the invention is a thermochromic ink comprising a thermochromic liquid crystalline medium as described above encapsulated in a light transmissive polymeric material, such as a continuous polymer matrix or polymer microcapsules.

Another object of the invention is the use of a thermochromic medium or thermochromic ink in decorative applications like pigments, inks and paints, cosmetics, thermodiagnostic applications like medical thermography, thermometry, optical and electrooptical applications, and security applications and devices.

Another object of the invention is a security marking or device comprising a thermochromic liquid crystalline medium or thermochromic ink according to the present invention.

Another object of the invention is a document of value comprising a security marking or device comprising a thermochromic medium or ink according to the present invention.

Another object of the invention is a security marking or device comprising two thermochromic liquid crystalline media or thermochromic inks that differ in their chirality to produce a hidden effect, and a document of value comprising such a security marking.

Another object of the invention is a security marking or device comprising two thermochromic liquid crystalline media or thermochromic inks according to the present invention that differ in the chirality of their chiral component, and preferably are identical otherwise.

Upon further study of the specification and appended claims, further objects and advantages of this invention will become apparent to those skilled in the art.

In the foregoing and the following, the term 'chiral compound' or 'chiral dopant', unless stated otherwise, means an optically active compound having a chiral center and inducing a helical twist of a single handedness in the host mixture, these terms including enantiomeric pure compounds and non-racemic mixtures of two enantiomers, i.e. mixtures with an excess of one enantiomer.

The term 'mesogenic compounds' in the foregoing and the following should denote compounds with a rod-shaped, board-shaped or disk-shaped mesogenic group, i.e. a group with the ability to induce mesophase behaviour. These compounds do not necessarily have to exhibit mesophase behaviour by themselves. It is also possible that these compounds show mesophase behaviour only in mixtures with other compounds or when the mesogenic compounds or the mixtures comprising them are polymerized. Rod-shaped and board-shaped mesogenic groups are especially preferred.

In order to exhibit thermochromic behaviour, the inventive medium has to exhibit a cholesteric phase and an underlying smectic phase, i.e. a smectic phase below the temperature range of the cholesteric phase. This is realized by using a host mixture with a nematic phase and an underlying smectic phase. Especially preferred is a host mixture with a nematic phase and an underlying smectic A phase.

One aspect of the invention is the finding that, by adding an optically active component comprising one or more chiral compounds with a high HTP already in small amounts to a liquid crystal host mixture, it is possible to obtain a thermochromic medium with a colour play over a wide temperature range including room temperature.

Especially preferred are chiral compounds with a HTP of 20 $\mu m^{-1}$ or more, with the total amount of these compounds being preferably less than 25% by weight of the total medium.

Since lower amounts of chiral dopant are needed, the dopants have less influence on the liquid crystal properties of the host mixture, compared to prior art mixtures. Therefore, the dopants do not necessarily have to be liquid crystalline or mesogenic themselves, which allows a broader choice of suitable chiral materials.

Furthermore, since smaller amounts of chiral compounds are needed in the inventive thermochromic media, problems occurring due to low solubility of the chiral compounds in the host mixture are reduced or even circumvented. Thus, the inventive media are more stable against partial or total crystallization or precipitation of the chiral components especially at low temperatures.

Furthermore, due to the reduced influence of the chiral dopants on the host mixture, it is possible to select the dopants and the host material independently of each other. Thus, in the inventive thermochromic media it is possible to vary the width of the temperature range of thermochromic colour play by appropriate selection of the dopants, and independently thereof to vary the position of the temperature range of thermochromic colour play by appropriate selection of the host mixture.

For example, by increasing the HTP of the chiral dopants in an inventive thermochromic medium, the temperature range over which the change of the reflection colour of the medium is observed is increasing. On the other hand, by using a host mixture with a lower smectic-nematic phase transition temperature, the entire range over which a change of the reflection colour of the medium is observed is shifted to lower temperatures.

The helical pitch and thus the reflection wavelength at a given temperature of an inventive thermochromic medium can be controlled by varying the total ratio of achiral and chiral compounds in the medium. With increasing ratio of chiral compounds the pitch and the reflection wavelength are decreasing.

Preferably the inventive thermochromic medium exhibits a negative temperature dependence of the pitch, i.e. the pitch decreases with increasing temperature.

A first preferred embodiment of the invention relates to a thermochromic liquid crystalline medium wherein the change $\Delta\lambda/\Delta T$ of the central wavelength of reflection $\Delta\lambda$ over a given temperature range $\Delta T$ is preferably >10 nm/° C., very preferably >30 nm/° C. A second preferred embodiment relates to a thermochromic liquid crystalline medium wherein the change $\Delta\lambda/\Delta T$ of the central wavelength of reflection $\Delta\lambda$ over a given temperature range $\Delta T$ is preferably <10 nm/° C., very preferably <5 nm/° C.

Another preferred embodiment relates to a thermochromic liquid crystalline medium wherein the central wavelength of selective reflection shows a change of at least 100 nm upon a change of the temperature over a range of at most 40° C., in particular of at most 25° C., very preferably of at most 10° C., most preferably of at most 5° C.

Another preferred embodiment relates to a thermochromic liquid crystalline medium wherein the liquid crystalline host mixture has a smectic—nematic phase transition temperature in the range from 0 to 60° C., in particular from 0 to 50° C., in particular from 0 to 40° C.

Another preferred embodiment relates to a thermochromic liquid crystalline medium wherein the optically active component comprises at least one chiral dopant having an HTP of at least 35 $\mu m^{-1}$, in particular of at least 45 $\mu m^{-1}$.

Preferably the liquid crystalline host mixture comprises one or more compounds of formula I

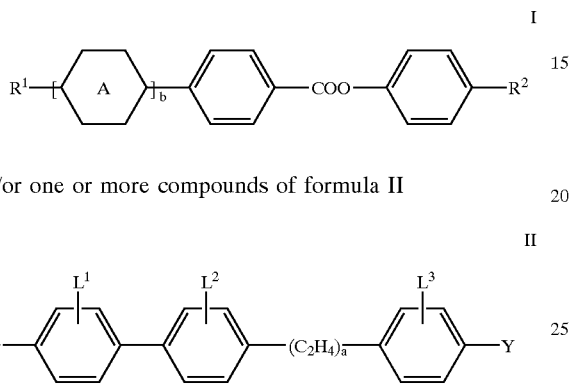

and/or one or more compounds of formula II

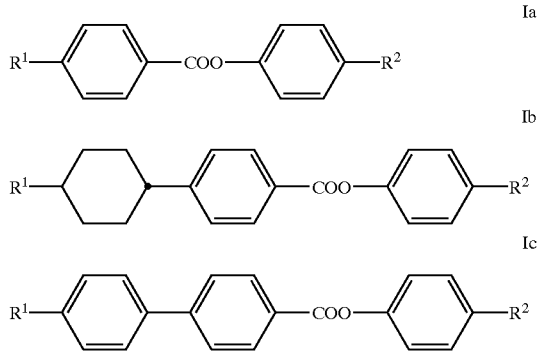

wherein
$R^1$ and $R^2$ are in each case independently an alkyl radical having up to 15 C atoms which is unsubstituted or substituted by halogen, it also being possible for one or more $CH_2$ groups to be replaced, in each case independently of one another, by —O—, —CH=CH—, —CO—, —CO—O— or —O—CO— in such a manner that oxygen atoms are not linked directly to one another,
a, b are independently 0 or 1,
$L^1$, $L^2$ and $L^3$ are independently of each other H, F or Cl,
Y is F, Cl or CN, and
A is trans-1,4-cyclohexylene or optionally fluorinated 1,4-phenylene.

The compounds of formula I are preferably selected from those of the following formulae Ia Ib Ic wherein $R^1$ and $R^2$ have the meanings given in formula I.
Especially preferred are compounds of formula Ia and Ib.
Particularly preferably the host mixture comprises one or more compounds, in particular one to five compounds of each formula Ia and formula Ib.

The compounds of formula II are preferably selected from the following formulae

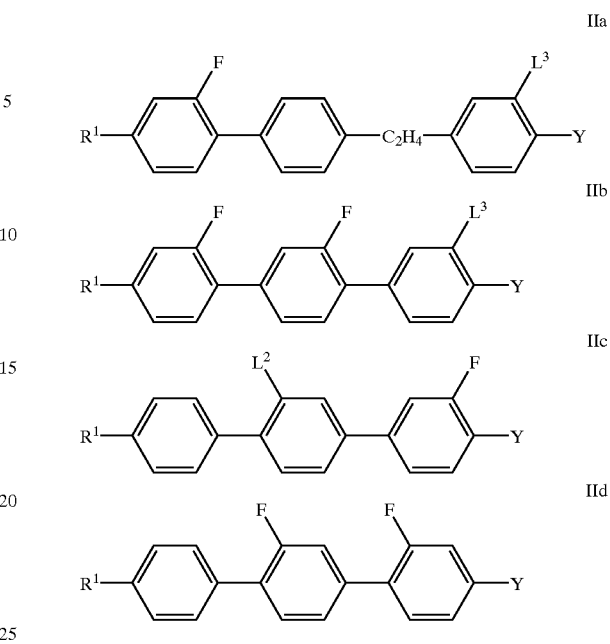

wherein $R^1$, Y, $L^2$ and $L^3$ have the meaning of formula II.

Particularly preferred are the compounds of formula IIa, IIb and IIc wherein Y is Cl and compounds of formula IId wherein Y is F. Further preferred are compounds of formula IIa wherein $L^3$ is H.

Particularly preferably the host mixture comprises one to four compounds of formulae IIa to IId.

Preferably the host mixture comprises one or more compounds of formula I and one or more compounds of formula II. Preferably the host mixture additionally comprises one or more four-ring compounds selected from the group comprising of those of formulae III-1 to III-7:

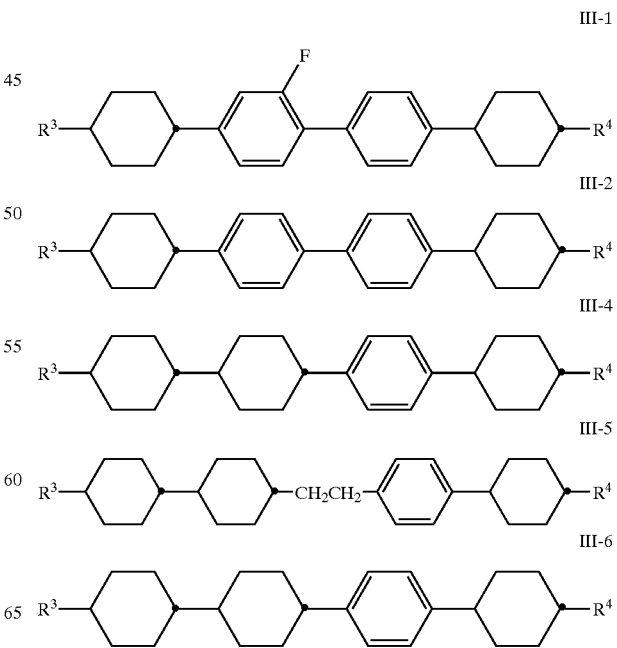

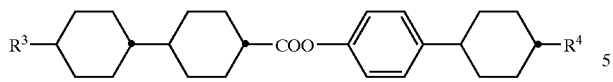

wherein $R^3$ and $R^4$ have one of the meanings of R, and the 1,4-phenylene groups may each, independently of one another, also be mono- or polysubstituted by fluorine.

Especially preferred are compounds of formula III-1 and III-2, in particular compounds of formula III-1.

Preferred embodiments of the present invention relate to host mixtures that contain:
  one to five compounds of formula Ia, one to four compounds of formula Ib, one to three compounds of formula Ia, and one to three compounds of formula III-1.
  10 to 70%, preferably 25 to 55% by weight of one or more compounds of formula Ia.
  5 to 45%, preferably 10 to 35% by weight of one or more compounds of formula Ib.
  5 to 35%, preferably 8 to 25% by weight of one or more compounds of formula II; and/or
  2 to 30%, preferably 2 to 15% by weight of one or more compounds of formula III-1.

Very preferably the thermochromic media comprise one or more compounds with high Δn, as these give particularly bright reflection colours according to equation (2) above. Especially preferred high An compounds are liquid crystalline or mesogenic tolanes and terphenyls.

Preferably the thermochromic liquid crystalline medium comprises 1 to 25%, in particular 2 to 15%, very preferably 3 to 10% by weight of an optically active component comprising one or more chiral dopants. The optically active component comprises preferably one to five, in particular one, two or three chiral dopants.

The chiral dopants are preferably selected from compounds with a high HTP of at least 20 $\mu m^{-1}$. Especially preferably the chiral dopants are selected of the following formulae, including the (R,S), (S,R), (R,R) and (S,S) enantiomers not shown

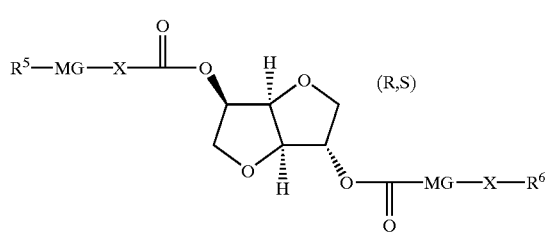

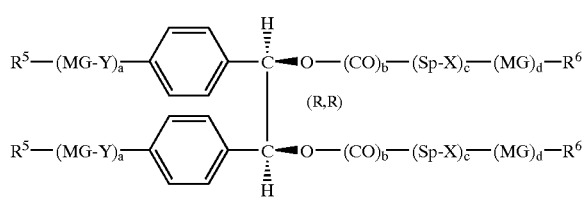

wherein
$R^5$ and $R^6$ are independently of each other a straight-chain or branched alkyl radical with up to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or, in case of formula V, $R^5$ may also denote H.

MG is in each case independently a mesogenic group,
X in each case independently denotes —O—, —S—, —CO—, —COO—, —OCO—, —OCO—O—, —CO—NH—, —NH—CO—, —O$CH_2$—, —$CH_2$O—, —S$CH_2$—, —$CH_2$S— or a single bond,
Y in each case independently denotes —O—, —S—, —CO—, —COO—, —OCO—, —CO—NH—, —NH—CO—, —$CH_2CH_2$—, —O$CH_2$—, —$CH_2$O—, —S$CH_2$—, —$CH_2$S—, —CH=CH—, —CH=CH—COO—, —OCO—CH=CH—, —C≡C— or a single bond,
Sp in each case independently denotes a spacer group with up to 20 C atoms,
a, b, c and d are independently of each other 0 or 1, with a+d being different from 0.

Examples of compounds of formula IV and their synthesis are described in WO 98/00428, the entire disclosure of which is incorporated into this application by way of reference. Examples of compounds of formula V and their synthesis are described in GB 2,328,207, the entire disclosure of which is incorporated into this application by way of reference.

MG in formula IV and V is preferably selected from the groups of formula VI

            VI wherein
$Z^1$ and $Z^2$ are each independently —COO—, —OCO—, —$CH_2CH_2$—, —O$CH_2$—, —$CH_2$O—, —CH=CH—, —CH=CH—COO—, —OCO—CH=CH—, —C≡C—, or a single bond,
$A^1$, $A^2$ and $A^3$ are each independently 1,4-phenylene in which, in addition, one or more CH groups may be replaced by N, 1,4-cyclohexylene in which, in addition, one or two non-adjacent $CH_2$ groups may be replaced by O and/or S, 1,4-cyclohexenylene, 1,4-bicyclo(2,2,2) octylene, piperidine-1,4-diyl, naphthalene-2,6-diyl, decahydronaphthalene-2,6-diyl, or 1,2,3,4-tetrahydro-naphthalene-2,6-diyl, it being possible for all these groups to be unsubstituted, mono- or polysubstituted with F, Cl, OH, CN, $NO_2$ or alkyl, alkoxy or alkanoyl groups having 1 to 7 C atoms wherein one or more H atoms may be substituted by F or Cl, and
m is 0, 1 or 2.

A smaller group of preferred mesogenic groups MG is listed below. For reasons of simplicity, Phe in these groups is 1,4-phenylene, PheL is a 1,4-phenylene group which is substituted by 1 to 4 groups L, with L being F, Cl, CN, OH, $NO_2$ or an optionally fluorinated alkyl, alkoxy or alkanoyl group with 1 to 7 C atoms, and Cyc is 1,4-cyclohexylene. The following list of preferred mesogenic groups comprises the subformulae VI-1 to VI-25 and their mirror images

| | |
|---|---|
| -Phe-Z-Phe- | VI-1 |
| -Phe-Z-Cyc- | VI-2 |
| -Cyc-Z-Cyc- | VI-3 |

| | |
|---|---|
| -PheL-Z-Phe- | VI-4 |
| -PheL-Z-Cyc- | VI-5 |
| -PheL-Z-PheL- | VI-6 |
| -Phe-Z-Phe-Z-Phe- | VI-7 |
| -Phe-Z-Phe-Z-Cyc- | VI-8 |
| -Phe-Z-Cyc-Z-Phe- | VI-9 |
| -Cyc-Z-Phe-Z-Cyc- | VI-10 |
| -Phe-Z-Cyc-Z-Cyc- | VI-11 |
| -Cyc-Z-Cyc-Z-Cyc- | VI-12 |
| -Phe-Z-Phe-Z-PheL- | VI-13 |
| -Phe-Z-PheL-Z-Phe- | VI-14 |
| -PheL-Z-Phe-Z-Phe- | VI-15 |
| -PheL-Z-Phe-Z-PheL- | VI-16 |
| -PheL-Z-PheL-Z-Phe- | VI-17 |
| -PheL-Z-PheL-Z-PheL- | VI-18 |
| -Phe-Z-PheL-Z-Cyc- | VI-19 |
| -Phe-Z-Cyc-Z-PheL- | VI-20 |
| -Cyc-Z-Phe-Z-PheL- | VI-21 |
| -PheL-Z-Cyc-Z-PheL- | VI-22 |
| -PheL-Z-PheL-Z-Cyc- | VI-23 |
| -PheL-Z-Cyc-Z-Cyc- | VI-24 |
| -Cyc-Z-PheL-Z-Cyc- | VI-25 |

Particularly preferred are the subformulae VI-1, VI-2, VI-4, VI-6, VI-7, VI-8, VI-11, VI-13, VI-14, VI-15 and VI-16.

In these preferred groups Z in each case independently has one of the meanings of $Z^1$ as given in formula I. Preferably Z is —COO—, —OCO—, —CH$_2$CH$_2$—, —C≡C— or a single bond.

Very preferably MG is selected from the following formulae and their mirror images

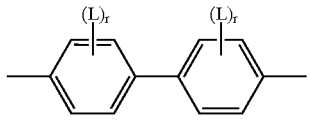

VIa

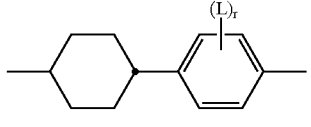

VIb

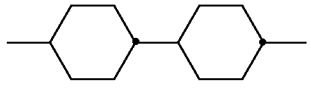

VIc

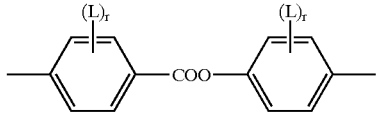

VId

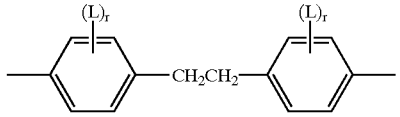

VIe

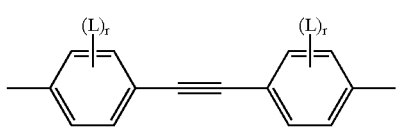

VIf

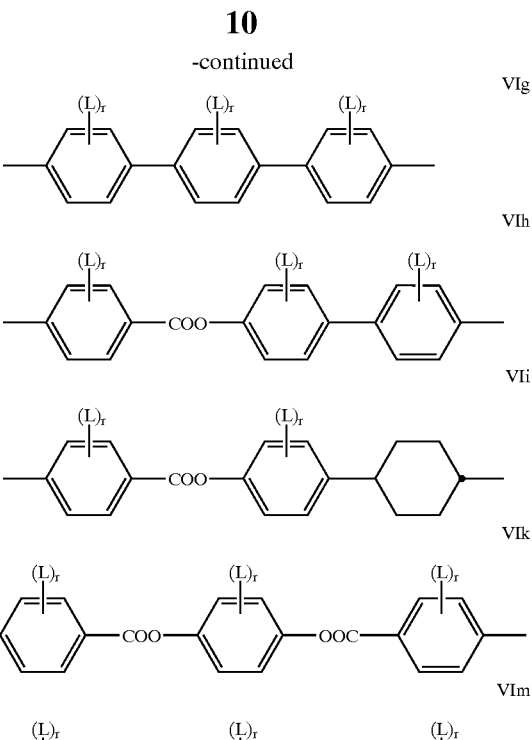

wherein L has the meaning given above and r is 0, 1 or 2.
The group

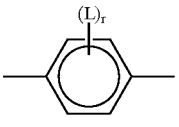

in these preferred formulae is very preferably

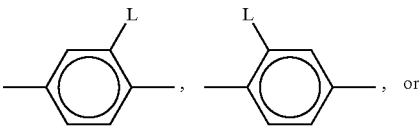

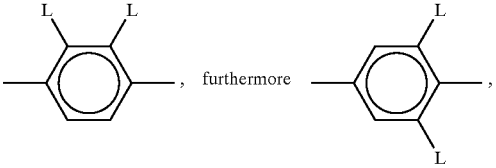

with L having each independently one of the meanings given above.

Particularly preferred are the subformulae VId, VIg, VIh, VIi, VIk and VIo, in particular the subformulae VId and VIk. L is preferably F, Cl, CN, OH, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, Cl, $CH_3$, $OCH_3$ and $COCH_3$.

$R^5$ and $R^6$ in formula IV and V are preferably F, Cl, CN, $OCF_3$, alkyl or alkoxy with 1 to 12 C atoms.

In case a in formula V is 0, $R^5$ is preferably H.

If $R^5$ or $R^6$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In the compounds of formula IV and V $R^5$ and $R^6$ may be an achiral or a chiral group. In case of a chiral group they are preferably selected according to the following formula VII:

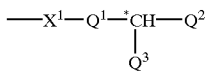

VII wherein
X$^1$ is —O—, —S—, —CO—, —COO—, —OCO—, —OCOO— or a single bond,
Q$^1$ is alkylene or alkylene-oxy with 1 to 10 C atoms or a single bond,
Q$^2$ is an alkyl or alkoxy group with 1 to 10 C atoms which may be unsubstituted, mono- or polysubstituted by halogen or CN, it being also possible for one or more non-adjacent $CH_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not linked directly to one another,
Q$^3$ is halogen, a cyano group or an alkyl or alkoxy group with 1 to 4 C atoms different from Q$^2$.

In case Q$^1$ in formula VII is an alkylene-oxy group, the O atom is preferably adjacent to the chiral C atom.

Preferred chiral groups $R^5$ and $R^6$ are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy for example.

As for the spacer group Sp in formula V all groups can be used that are known for this purpose to the skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N(CH$_3$)—, —CO—, —O—CO—, —S—CO—, —O—COO—, —CO—S—, —CO—O—, —CH (halogen)-, —CH(CN)—, —CH=CH— or —C≡C—.

Typical spacer groups are for example —(CH$_2$)$_o$—, —(CH$_2$CH$_2$O)$_p$—CH$_2$CH$_2$—, —CH$_2$CH$_2$—S—CH$_2$CH$_2$— or —CH$_2$CH$_2$—NH—CH$_2$CH$_2$—, with o being an integer from 2 to 12 and p being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene, 1-methylalkylene, ethenylene, propenylene and butenylene for example.

Especially preferred are inventive compounds of formula V wherein Sp is denoting an alkyl or alkoxy group with 2 to 8 C atoms. Straight-chain alkyl or alkoxy groups are especially preferred.

In another preferred embodiment of the invention the chiral compounds of formula V comprise at least one spacer group Sp that is a chiral group of the formula VIII:

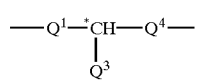

VIII wherein

Q$^1$ and Q$^3$ have the meanings given in formula VII, and
Q$^4$ is an alkylene or alkylene-oxy group with 1 to 10 C atoms or a single bond, being different from Q$^1$.

Especially preferred are chiral dopants selected from the following formulae

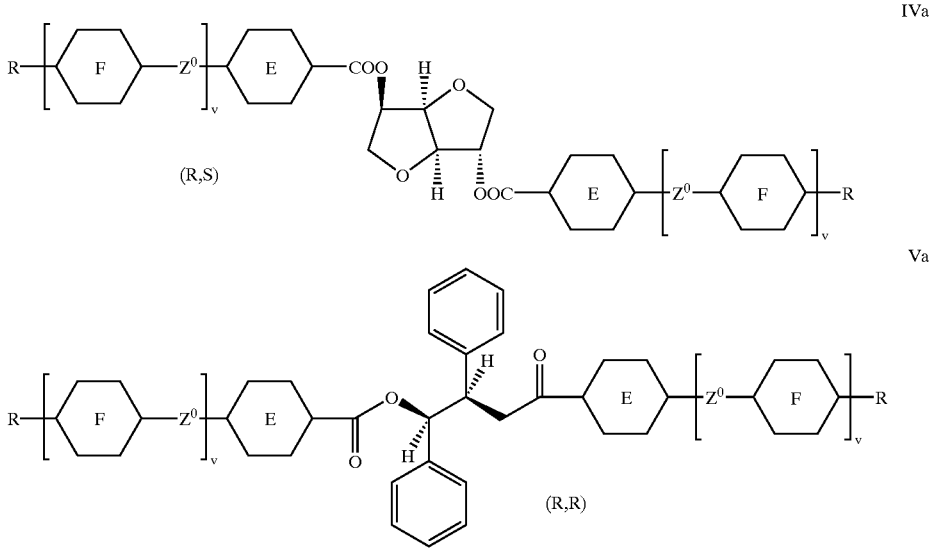

including the (R,S), (S,R), (R,R) and (S,S) enantiomers not shown,
wherein E and F are each independently trans-1,4-cyclohexylene or unsubstituted or mono- or difluorinated 1,4-phenylene, v is 0 or 1, Z° is —COO—, —OCO—, —CH$_2$CH$_2$— or a single bond, and R is alkyl, alkoxy or alkylcarbonyl, alkoxycarbonyl or alkoxycarbonyloxy with 1 to 12 C atoms.

The above chiral compounds of formula IV and V exhibit a very high helical twisting power (HTP), and are therefore particularly useful for the purpose of the present invention.

In a preferred embodiment of the present invention, the thermochromic medium, in addition to the chiral dopants with high HTP, comprises one or more conventional chiral dopants, like for example the commercially available R/S 811, R/S 1011, R/S 2011 or CB 15 (from Merck KGaA, Darmstadt, Germany), for fine tuning of the colour play achieved by the high HTP dopants.

The inventive thermochromic liquid crystalline medium can be microencapsulated in a light transmissive polymer material to give discrete, free microcapsules, which can be used for example as a slurry or dispersed in a binder system to give a thermocromic ink. Alternatively, the inventive thermochromic medium can be embedded in form of microdroplets in a continuous transparent polymer matrix, like for example a PDLC film (polymer dispersed liquid crystal) or an NCAP film (nematic curvilinear aligned phase).

The above methods of encapsulation are known to the expert and have been described in prior art. Suitable methods of encapsulation are disclosed e.g. in U.S. Pat. Nos. 3,585,381, 4,435,047, 4,688,900, 5,202,063, EP 0 571 550, DE 40 17 212, DE 41 40 151, EP 0 564 959 and GB 2 280 681, the entire disclosure of these documents being incorporated into this application by reference.

The thermochromic media and inks according to the present invention can be used in a wide range of applications, including pigments, inks or paints for decorative applications, cosmetics, thermodiagnostic applications like medical thermography, thermometry, optical and electrooptical applications, and security applications and devices.

For example, an inventive thermochromic medium or ink can be used in thermometry or biomedical thermography as a diagnostic aid, e.g. for breast cancer detection or placental location.

An inventive thermochromic medium or ink can also be used for the preparation of effect pigments for decorative, cosmetic or security applications. The preparation of thermochromic pigments is described for example in WO 93/12195 and EP 0 357 844. The effect pigment can be used as colourant in lacquer compositions, plastic compositions, dyed filter compositions, dyed glass compositions, dyed cosmetic compositions, printing ink compositions, and in cosmetic preparations like e.g make-up or hair colouring agents.

The inventive thermochromic media and inks can also be used for the preparation of electrooptical displays, for example PDLC displays, or optical elements like colour filters or notch polarizers.

Especially preferred is the use of inventive thermochromic media and inks in security applications and devices, where they can form e.g. a visible image due to a colour change when subjected to a temperature change, or show an iridescent colour effect that cannot be counterfeited by copying. For example, the thermochromic media and inks can be used as security marking on forgery proof security documents such as credit cards, identity cards, banknotes etc., where they are applied e.g. as a thin layer or in form of an image or pattern on the document, and reveal an underlying message or information on the document when subjected to a temperature change, or exhibit a colour effect that is difficult to counterfeit e.g. when copying the document.

The invention also relates to a security marking comprising an inventive thermochromic medium or ink, and to a document of values, like a credit card, identity card or banknote, comprising such a security marking.

It is also possible in the above applications to combine the inventive thermochromic media and inks with conventional absorption pigments, dyestuffs, or other thermochromic or photochromic materials, and to apply additional decorative or identification techniques like holograms or embossed surfaces.

The entire disclosure of all applications, patents and publications, cited above or below, and of corresponding European application No. EP 99 116 850.1, filed Sep. 3, 1999, is hereby incorporated by reference.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

EXAMPLES

In the foregoing and in the following examples, unless otherwise indicated, all temperatures are set forth uncorrected in degrees Celsius and all parts and percentages are by weight.

The following abbreviations are used to illustrate the liquid crystalline phase behaviour of the compounds:

K=crystalline; N=nematic; S=smectic; Ch=cholesteric; I=isotropic. The numbers between the symbols indicate the phase transition temperatures in ° C.

Example 1

The following thermochromic liquid crystal mixture was formulated

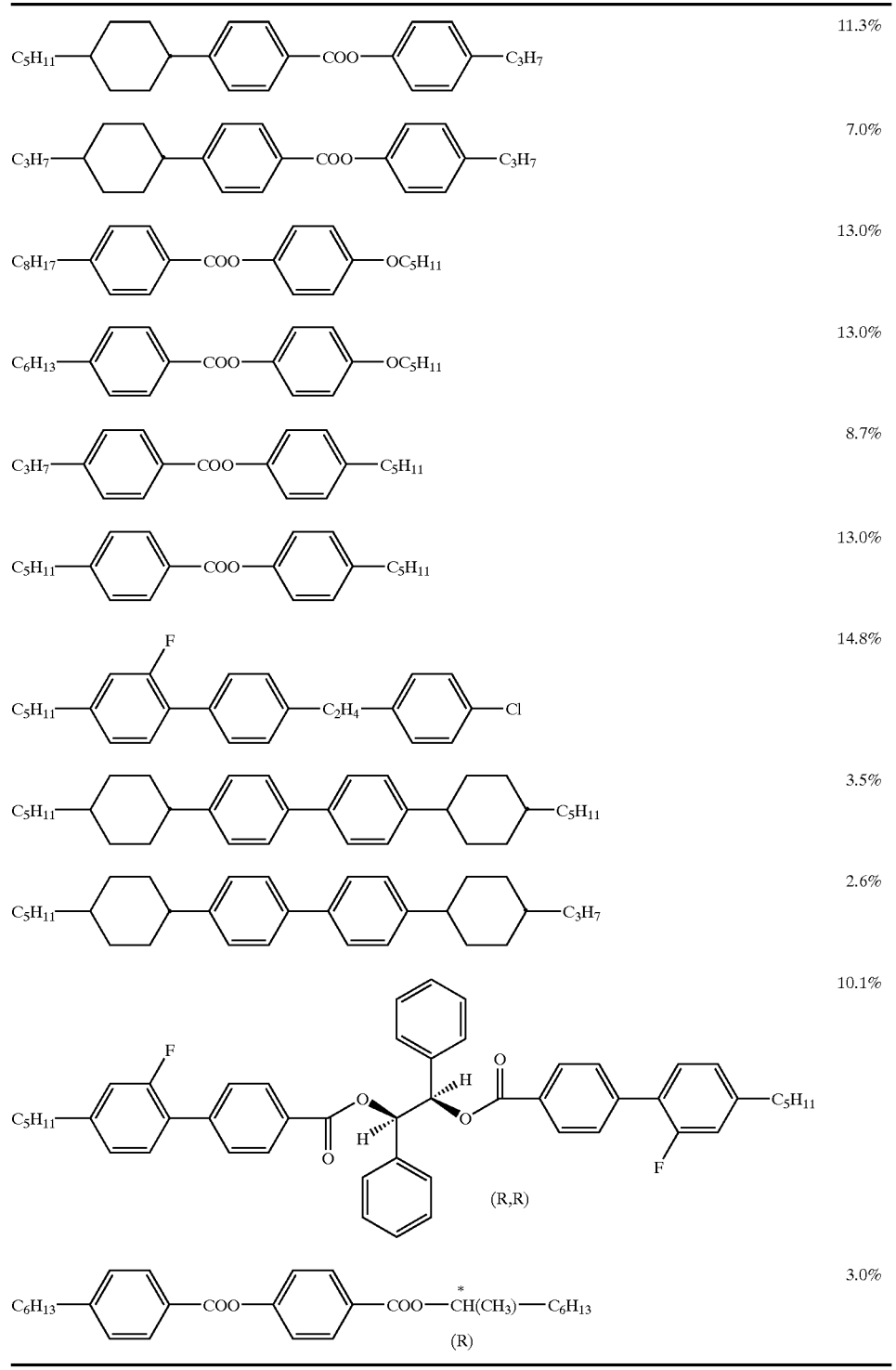

The thermochromic medium exhibits a colourplay of the reflection colour from red (600 nm) at 30° C. through yellow and green to light blue (480 nm) at 40° C.

Example 2

The following thermochromic liquid crystal mixture was formulated

| Compound | % |
|---|---|
| $C_5H_{11}$—[Cy]—[Ph]—COO—[Ph]—$C_3H_7$ | 11.8% |
| $C_3H_7$—[Cy]—[Ph]—COO—[Ph]—$C_3H_7$ | 7.3% |
| $C_8H_{17}$—[Ph]—COO—[Ph]—$OC_5H_{11}$ | 13.8% |
| $C_6H_{13}$—[Ph]—COO—[Ph]—$OC_5H_{11}$ | 13.8% |
| $C_3H_7$—[Ph]—COO—[Ph]—$C_5H_{11}$ | 9.5% |
| $C_5H_{11}$—[Ph]—COO—[Ph]—$C_5H_{11}$ | 13.7% |
| $C_5H_{11}$—[Ph(2-F)]—[Ph]—$C_2H_4$—[Ph]—Cl | 15.0% |
| $C_5H_{11}$—[Cy]—[Ph]—[Ph]—[Cy]—$C_5H_{11}$ | 3.5% |
| $C_5H_{11}$—[Cy]—[Ph]—[Ph]—[Cy]—$C_3H_7$ | 2.6% |
| Chiral diester (R,R) with $C_5H_{11}$-biphenyl(2-F) groups | 9.0% |

The thermochromic medium exhibits a colour play of the reflection colour from red (600 nm) at 27° C. through yellow and green to light blue (480 nm) at 65° C.

Example 3

The following thermochromic liquid crystal mixtures were formulated

Mixture 3a:

| Structure | % |
|---|---|
| $C_5H_{11}$—(cyclohexyl)—(phenyl)—COO—(phenyl)—$C_3H_7$ | 7.0% |
| $C_3H_7$—(cyclohexyl)—(phenyl)—COO—(phenyl)—$C_3H_7$ | 3.0% |
| $C_8H_{17}$—(phenyl)—COO—(phenyl)—$OC_5H_{11}$ | 13.0% |
| $C_6H_{13}$—(phenyl)—COO—(phenyl)—$OC_5H_{11}$ | 13.0% |
| $C_3H_7$—(phenyl)—COO—(phenyl)—$C_5H_{11}$ | 10.0% |
| $C_5H_{11}$—(phenyl)—COO—(phenyl)—$C_5H_{11}$ | 25.0% |
| $C_5H_{11}$—(2-F-phenyl)—(phenyl)—$C_2H_4$—(phenyl)—Cl | 12.0% |
| $C_5H_{11}$—(cyclohexyl)—(phenyl)—(phenyl)—(cyclohexyl)—$C_5H_{11}$ | 2.0% |
| $C_5H_{11}$—(cyclohexyl)—(phenyl)—(phenyl)—(cyclohexyl)—$C_3H_7$ | 2.0% |
| $C_5H_{11}$—(cyclohexyl)—(phenyl)—COO—CH(Ph)—CH(Ph)—OOC—(phenyl)—(cyclohexyl)—$C_5H_{11}$ (S,S) | 5.0% |
| $C_6H_{13}$—(phenyl)—COO—(phenyl)—COO—*CH($CH_3$)—$C_6H_{13}$ (R) | 2.75% |

-continued
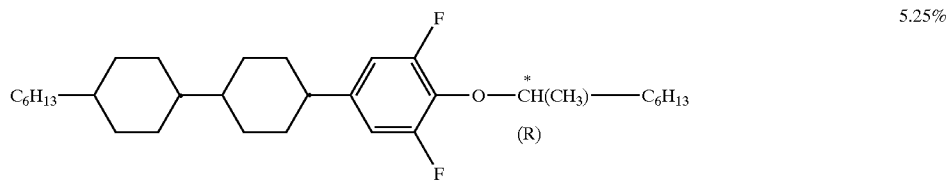 5.25%
Mixture 3b:
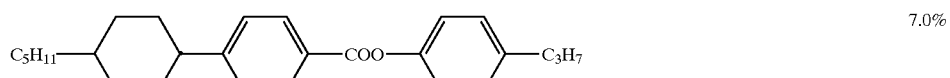 7.0%
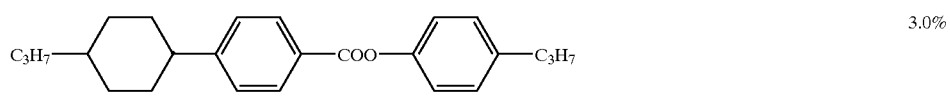 3.0%
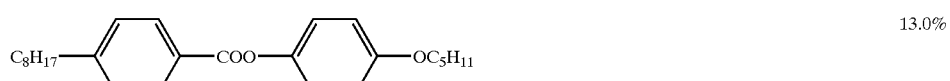 13.0%
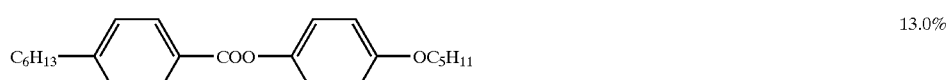 13.0%
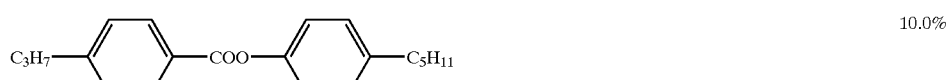 10.0%
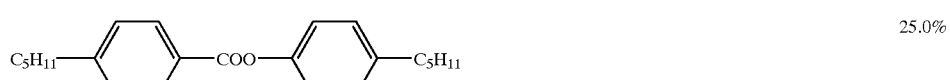 25.0%
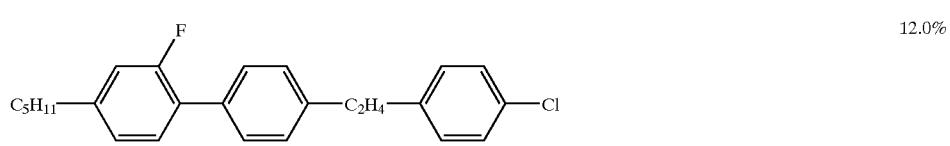 12.0%
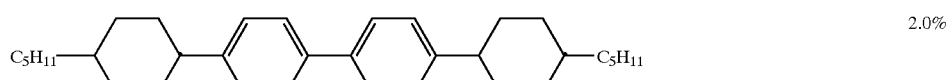 2.0%
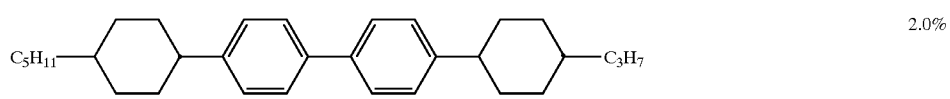 2.0%
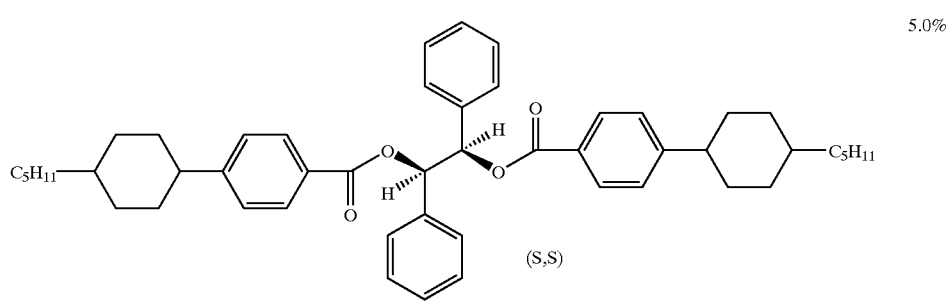 5.0%

-continued

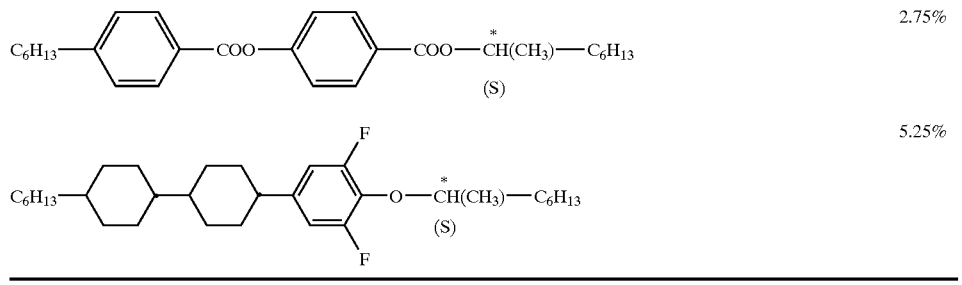

2.75%

5.25%

Both thermochromic media 3a and 3b exhibit a colourplay of the reflection colour from red (600 nm) at 30° C. through yellow and green to blue (480 nm) at 40° C. The handedness of the reflected circularly polarised light is different for the mixtures 3a and 3b.

The preceding examples can be repeated with similar success by substituting the generically or specifically described reactants and/or operating conditions of this invention for those used in the preceding examples.

From the foregoing description, one skilled in the art can easily ascertain the essential characteristics-of this invention, and without departing from the spirit and scope thereof, can make various changes and modifications of the invention to adapt it to various usages and conditions.

What is claimed is:

1. A thermochromic liquid crystalline medium comprising a liquid crystalline host mixture and an optically active component, wherein the liquid crystalline host mixture has a smectic—nematic phase transition temperature in the range from 0 to 60° C and the optically active component comprises at least one chiral dopant with a helical twisting power (HTP) of at least 20 $\mu m^{-1}$.

2. A thermochromic liquid crystalline medium according to claim 1, wherein the medium has a central wavelength of selective reflection showing a change of 120 nm upon a change of the temperature over a range of 10° C. or less.

3. A thermochromic liquid crystalline medium according to claim 1, wherein the medium has a central wavelength of selective reflection showing a change of 120 nm upon a change of the temperature over a range of more than 10° C.

4. A thermochromic liquid crystalline medium according to claim 1, wherein the liquid crystalline host mixture has a smectic—nematic phase transition temperature in the range from 0 to 40° C.

5. A thermochromic liquid crystalline medium according to claim 1, wherein the optically active component comprises at least one chiral dopant having an HTP of at least 35 $\mu m^{-1}$.

6. A thermochromic liquid crystalline medium according to claim 1, wherein the liquid crystalline host mixture comprises one or more compounds of formula I

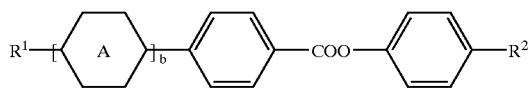

I and one or more compounds of formula II

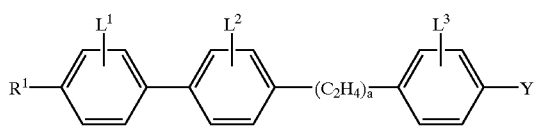

II wherein
R$^1$ and R$^2$ are in each case independently an alkyl radical having up to 1 to 15 C atoms which is unsubstituted or substituted by halogen, it also being possible for one or more CH$_2$ groups to be replaced, in each case independently of one another, by —O—, —CH=CH—, —CO—, —CO—O— or —O—CO— in such a manner that oxygen atoms are not linked directly to one another,
a, b are independently 0 or 1,
L$^1$, L$^2$ and L$^3$ are independently of each other H, F or Cl,
Y is F, Cl or CN, and
A is trans-1,4-cyclohexylene or optionally fluorinated 1,4-phenylene.

7. A thermochromic liquid crystalline medium according to claim 1, wherein the optically active component comprises at least one chiral dopant selected from those of the following formulae IV and V, including the (R.S), (S,R), (R,R), (S,S) enantiomers not shown

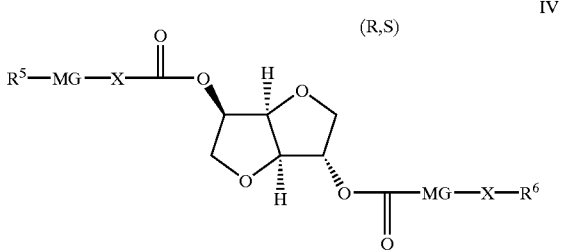

IV

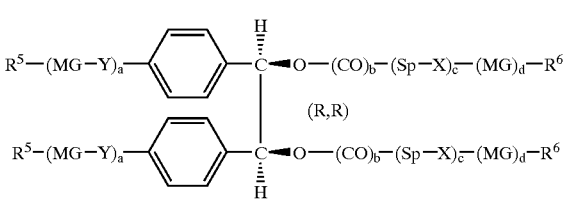

V wherein
R$^5$ and R$^6$ are independently of each other a straight-chain or branched alkyl radical with up to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or, in case of formula V, $R^1$ may also denote H, MG is in each case independently a mesogenic group, X in each case independently denotes —O—, —S—, —CO—, —COO—, —OCO—, —OCO—O—, —CO—NH—, —NH—CO—, —$OCH_2$—, —$CH_2O$—, —$SCH_2$—, —$CH_2S$— or a single bond, Y in each case independently denotes —O—, —S—, —CO—, —COO—, —OCO—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C— or a single bond, Sp in each case independently denotes a spacer group with up to 20 C atoms, a, b, c and d are independently of each other 0 or 1, with a+d being different from 0.

8. A thermochromic liquid crystalline medium according to claim 5, wherein the liquid crystalline host mixture comprises one or more compounds of formula I

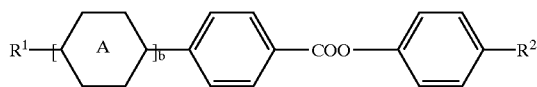

I and one or more compounds of formula II

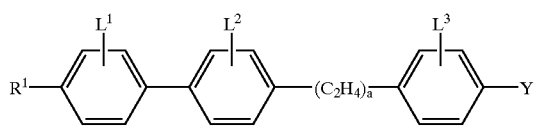

II wherein $R^1$ and $R^2$ are in each case independently an alkyl radical having up to 1 to 15 C atoms which is unsubstituted or substituted by halogen, it also being possible for one or more $CH_2$ groups to be replaced, in each case independently of one another, by —O—, —CH=CH—, —CO—, —CO—O— or —O—CO— in such a manner that oxygen atoms are not linked directly to one another, a, b are independently 0 or 1, $L^1$, $L^2$ and $L^3$ are independently of each other H, F or Cl, Y is F, Cl or CN, and A is trans-1,4-cyclohexylene or optionally fluorinated 1,4-phenylene.

9. A thermochromic ink comprising a thermochromic liquid crystalline medium according to claim 1, encapsulated in a light transmissive polymeric material.

10. A thermochromic ink comprising a thermochromic liquid crystalline medium according to claim 8, encapsulated in a light transmissive polymeric material.

11. A security marking or device comprising a thermochromic liquid crystalline medium according to claim 1.

12. A security marking or device comprising two thermochromic liquid crystalline media according to claim 1, which differ in their chirality.

13. A security marking or device comprising a thermochromic ink according to claim 9.

14. A security marking or device comprising two thermochromic inks according to claim 9 which differ in their chirality.

15. A document of value comprising a security marking or device according to claim 11.

16. A document of value comprising a security marking or device according to claim 12.

17. A document of value comprising a security marking or device according to claim 13.

18. A document of value comprising a security marking or device according to claim 14.

19. A method for providing a decorative effect and/or a thermodiagnostic effect in a composition which comprises incorporating a thermochromic liquid crystalline medium according to claim 1 in the composition.

20. A pigment comprising a thermochromic ink of claim 9.

21. An electrooptical display comprising a thermochromic liquid crystalline medium according to claim 1.

22. A color filter or notch polarizer comprising a thermochromic liquid crystalline medium according to claim 1.

* * * * *